United States Patent [19]
Elnagar et al.

[11] Patent Number: 5,900,512
[45] Date of Patent: May 4, 1999

[54] OXIDATION PROCESS

[75] Inventors: Hassan Y. Elnagar; Robert L. Davis, both of Baton Rouge, La.

[73] Assignee: Albemarle Corporation, Richmond, Va.

[21] Appl. No.: 08/927,657

[22] Filed: Sep. 11, 1997

[51] Int. Cl.[6] .................................................. C07F 9/53
[52] U.S. Cl. ............................................... 568/14; 568/27
[58] Field of Search ........................................ 568/14, 27

[56] References Cited

U.S. PATENT DOCUMENTS 5,141,652  8/1992  Moore, Jr. et al. ...................... 210/754

OTHER PUBLICATIONS

Kim, K.S. et al., "Tellurium Dioxide Catalyzed Selective Oxidation of Sulfides to Sulfoxides With Hydrogen Peroxide," *Tetrahedron Letters*, vol. 31, No. 20, pp. 2893–2894 (1990), Pergamon Press plc., London.

Kageyama, T., "Sodium Bromite: A New Selective Reagent for the Oxidation of Sulfides and Alcohols," *Synthesis* pp. 815–816 (1983).

Kalantar, T.H. et al., "Bromine As An Oxidant For Direct Conversion of Aldehydes to Esters*—Convenient One–Pot Conversion of Alcohols into Esters Via Hemiacetal Intermediates†,"—condensation and commentary—*Chemtracts—Organic Chemistry, Esters From Aldehydes and Alcohols,* pp. 119–120 (1989).

Tetrahedron, Konno, "Anodic generation of polybromochloride ions and their utilization as precisely controlled oxidizing regeants for ex–cell indirect eectrooxidation of alcohols", 42(4/5) 887–894, Jan. 1991.

Bull Chem Soc of Japan, "Cataytic Behavior of Sulfonium Trihalides in the Low–temperature Liquid–Phase Oxidation of Tetralin", OHkubo, 50(7), pp. 1883–1884, Jan. 1977.

Polymer International, Polyhalide Derivatives of Polystyene–based benyltriethylammonium Resins as Oxidizing Agents Mitra, 42 (2), pp. 173–178, Feb. 1997.

*Primary Examiner*—Gary Geist
*Assistant Examiner*—Jean F Vollano
*Attorney, Agent, or Firm*—E. E. Spielman, Jr.

[57] ABSTRACT

An oxidation process for organic compounds employs stabilized bromine chloride solutions as the oxidizing agent. Organic compounds which contain an oxidizable moiety, such as thioanisole and triphenylphosphine, are rapidly converted to sulfoxides and phosphine oxides, respectively, without over-oxidation.

18 Claims, No Drawings

OXIDATION PROCESS

TECHNICAL FIELD

This invention relates generally to the oxidation of organic compounds and, more specifically, to a process for the rapid and efficient oxidation of organic compounds, such as sulfides and phosphines, using a stabilized solution of bromine chloride as the oxidizing agent.

BACKGROUND

Many of the widely used oxidizing agents, (e.g., hydrogen peroxide and 3-chioroperbenzoic acid (m-CPBA)) cause over-oxidation of sulfides to sulfoxides and then to sulfones. Selective oxidation by hydrogen peroxide requires tellurium dioxide ($TeO_2$) to moderate its reactivity and avoid over-oxidation. The reaction takes several hours for completion (see K. S. Kim et al., *Tetrahedron Lett.* 1990, 2893). T. Kageyama in *Synthesis* 1983, 815, reports that sodium bromite ($NaBrO_2$) is a selective reagent for the oxidation of sulfides in aqueous dioxane. This reagent requires purification at low temperature and currently is not commercially available. T. H. Kalanter et al., *CHEMTRACTS* 1989, 2(2), 119, used halogen-alcohol in a bicarbonate buffer to oxidize a series of functionalized aldehydes to esters. Long reaction times were necessary. Stabilized bromine chloride prepared by combining aqueous halide salt solutions or hydrohalic acids with bromine chloride has been used as a biocide for water treatment (see U.S. Pat. No. 5,141,652).

We have now found that halide salt stabilized bromine chloride solutions are effective, stable, easy to store, and handle, selective oxidizing agents for organic compounds. The stabilized brornine chloride solutions can selectively and rapidly provide quantitative conversions of, for example, organic sulfides and phosphines to oxidized products.

SUMMARY OF INVENTION

In accordance with this invention, there is provided a process for oxidizing organic compounds comprising reacting an organic compound which contains an oxidizable moiety with an aqueous halide salt stabilized bromine chloride solution, so as to insert at least one oxygen atom into said oxidizable moiety.

Bromine chloride is typically prepared by reacting equimolar amounts of bromine and chlorine. Other known methods include the reaction of HCl gas with N-bromoacetamide or N-bromosuccinamide in halogenated solvents and the reaction of NaBr with chlorine or Chloramine-T in aqueous solutions.

The stabilized bromine chloride oxidizing reagent for use in the process of the invention includes a halide salt substituent and, optionally, a hydrohalic acid. The salt substituent comprises a halide anion and an alkali metal, alkaline earth metal, transition metal or quarternary ammonium cation. Preferably, the halide salt is selected from $CaBr_2$, $CaCl_2$, KBr, KCl, LiBr, LiCl, $MgCl_2$, $MgBr_2$, NaCl, NaBr, and the like, including mixtures thereof, with NaCl being a most preferred salt.

The oxidizing reagent can be formed by mixing the halide salt substituent and, optionally, a hydrohalic acid, (e.g., HCl, HBr, HI, and HF) with the bromine chloride by any conventional technique to form an aqueous solution of the ingredients. For example, bromine chloride can be sparged into an aqueous solution of the halide salt as a gas or mixed with the halide salt solution as a liquid. The bromine chloride is preferably used in proportions to provide from about 0.25 to 0.50 mole of bromine chloride per mole of halide salt. The aqueous, stabilized BrCl reagent preferably contains from about 5 to 20 weight %, and more preferably from about 12 to 17 weight %, of the bromine chloride ingredient. An especially preferred reagent is an aqueous $[Na^+(BrCl_2)^-]$ solution prepared by dissolving BrCl in an aqueous NaCl solution. The chloride ion helps to solubilize bromine chloride by complexation in water, i.e., an increase from about 8.5 weight % for BrCl to >15 weight % as the $[Na^+(BrCl_2)^-]$ complex.

The organic compounds which can be oxidized by the process of the invention include both aliphatic and aromatic compounds which contain an oxidizable moiety. Non-limiting examples of such moieties include groups which contain an heteroatom such as sulfur, phosphorous, oxygen, nitrogen, selenium, and the like. For example, sulfides, i.e., aryl thioethers such as PHSR, phosphines such as $Ph_3P$, aldehydes, aminos, selenides and benzylic alcohols, where Ph=phenyl or substituted phenyl and R is alkyl. The presence of electron donating groups in the phenyl ring accelerates the oxidation reaction. For example, the oxidation of methyl p-tolyl sulfide is three times as fast as thioanisole under similar conditions.

The stabilized bromine chloride reagents are also brominatin, agents. Competition between nuclear broid nation and oxidation of the heteroatom when reacting thioanisole with the BrCl reagent is solvent dependent. Accordingly, selective oxidation is achieved by the use of protic solvents such as alcohols or aqueous alcohols, due to the extremely fast oxidation rate in these solvents. Brorination of aromatic sulfides is favored by the use of anhydro us halogenated hydrocarbons with the oxidation reactions increasing as the polarity of the solvent increases. On the other hand, phosphines are rapidly and selectively oxidized by the BrCl reagent either in halogenated solvents, methanol or in a mixture of both. Non-limiting examples of solvents suitable for use in the oxidation process include methanol, ethylene dichloride, bromochloromethane, and the like, including mixtures thereof. The solvent system can be selected depending upon the moiety to be oxidized so as to favor either oxidation or a mixture of oxidation and bromination. Preferably, amounts of solvent of from about 10 to 90 weight percent of the total weight of reaction mixture are used.

The stabilized BrCl oxidizing agent is generally used in a stoichiometric amount up to about a 50 percent excess over the molar equivalent amount of oxygen to be added to the oxidizable moieties in the compound being oxidized.

The reaction temperatures preferably range from about 0° to 80° C. and more preferably are from about 10° to 40° C. The oxidation reactions are rapid and, in some cases, appear to be instantaneous, with little, if any, over-oxidation. Generally, the reactions are complete within 30 minutes to an hour, at or below ambient temperatures. In contrast, hydrogen peroxide-sodium hydroxide oxidations are reported to require heating overnight to obtain complete conversions. The reactants can be mixed in any order. Preferably, the stabilized bromine chloride reagent is added to a solvent mixture of the compound to be oxidized.

The invention is further illustrated by, but is not intended to be limited to, the following examples. The stabilized BrCl oxidizing reagent used in the examples is prepared by dissolving approximately 15 weight % of BrCl in a 3 molar aqueous NaCl solution. The BrCl is prepared by mixing equimolar amounts of bromine and chlorine. The solvents are Baker Analyzed Reagent grade unless otherwise noted. The reactions are monitored by GC using either a 15 m HP-1 column or a J&W 15 m DB-17HT polar column (I.D. 0.32 mm widepore). The structure of all products was determined from NMR, IR, and GC/MS analyses and by comparison with literature data.

The $^1$H-NMR spectra were obtained at 400 MHZ on a Bruker/GE Omega 400 WB or at 300 MHZ on a Bruker/GE spectrometer with deuterochloroforn as solvent and TMS as internal standard. The $^{13}$C-NMR spectra are obtained at 75.5 MHZ on the Bruker spectrometer QE-300. Mass spectra were obtained on a VG 70SE at 70 eV.

Unless otherwise noted, the reactions are carried out in 250-ml round bottom flasks equipped with an addition funnel, magnetic stirrer, stirring bar and ice bath.

EXAMPLE 1

A solution of thioanisole (2.48 g, 20 mmol) in methanol (100 mL) in a 250-mL flask was cooled in an ice bath. Stabilized BrCl solution (15 wt. % solution, 18 mL, ~28 mmol) was then added dropwise, with stirring. After the addition, the ice bath was removed, the reaction mixture was allowed to stand at room temperature and the progress of the reaction was monitored by gas chromatography (GC). In less than one hour, the starting material was totally converted to product and the orange-reddish solution turned light yellow. The reaction mixture was quenched with a few drops of sodium sulfite solution, diluted with ethylene dichloride (EDC, 100 mL), and washed with water (100 mL). After phase separation, the colorless organic layer was dried ($Na_2SO_4$) and concentrated under reduced pressure to furnish 2.44 g (~87% yield) of methyl phenyl sulfoxide as a colorless oil. GC analysis indicated the presence of ~2% of the corresponding sulfone.

EXAMPLE 2

A solution of methyl p-tolyl sulfide (2.77 g, 20 mmol) in methanol was cooled in an ice bath. Stabilized BrCl solution (15 wt. % solution, 17 mL, ~26 mmol) was then added dropwise, with stirring. The ice bath was removed and the reaction progress was monitored by GC. Approximately 95% conversion of the sulfide to the sulfoxide was detected within 30 minutes. A longer reaction time did not significantly improve the conversion. A total conversion to the sulfoxide product was obtained when an additional 1 mL of stabilized BrCl solution (total 18 mL, ~28 mmol) was added to the reaction mixture. Quenching with sulfite solution, diluting with EDC (150 mL), and washing with water (100 mL) furnished a colorless solution. The solution was dried ($Na_2SO_4$) and concentrated under reduced pressure to give 2.72 g (88% yield, >98% pure by GC) of a white solid identified as methyl p-tolyl sulfoxide.

EXAMPLE 3

Neomenthyldiphenylphosphine (3.24 g, 10 mmol) in a methanol-EDC mixture (100 mL, 50:50 Vol.) was placed in a 250-mL round bottom flask and cooled in an ice bath. Stabilized $BrCl_2$ (15 wt. % solution, 7 mL, ~11 mmol) was added dropwise to the homogeneous phosphine solution. The reddish-brown color of the BrCl solution disappeared instantaneously as it was added. An orange color persisted during the addition of the last 1 mL of the oxidizing reagent, indicating total conversion. The reaction mixture was quenched with a few drops of sodium sulfite and was totally decolorized. The reaction mixture was then diluted with EDC (50 mL) and washed with water (100 mL). A mixture of xylenes (50 mL) were added and the lighter organic solvents were removed under reduced pressure. The resulting xylene solution was allowed to stand overnight in the refrigerator and product crystals formed. The crystals were separated by filtration to obtain 1.86 g of product (100% pure by GC) as the first crop. A second crop of crystals (0.96 g, 99.3% pure) was obtained after evaporation of all the xylenes. A total of 2.82 g of neomenthyldiphenyl phosphine oxide (83%) was obtained.

EXAMPLE 4

A solution of triphenylphosphine (2.62 g, 10 mmol) in a methanol-EDC mixture (100 mL, 50:50, Vol.) was placed in a 250-mL round bottom flask and cooled in an ice bath. Stabilized BrCl (15 wt. % solution, 7.5 mL, 12 mmol) was added dropwise to the homogeneous phosphine solution. The reddish-brown color of the BrCl solution disappeared instantaneously as it was added. An orange color persisted during the addition of the last 0.5 mL, indicating total conversion. The reaction mixture was allowed to stand for 30 minutes at room temperature and then was quenched with a few drops of sodium sulfite solution which totally decolorized it. Dilution with EDC (100 mL) and washing with water (100 mL) was followed by phase separation. The organic layer was dried ($Na_2SO_4$) and concentrated to afford 2.64 g (95% yield) of triphenylphospine oxide as a white solid in 97% purity (3% starting material).

EXAMPLE 5

Oxidation versus Ring Bromination—Effect of Solvent Polarity on Selectivity

To each of four solutions of thioanisole (5 mmol) in 10 mL in four solvents of different polarity were added limited amounts of about 2 mL of 15 wt. % stabilized BrCl reagent. The reaction mixtures were analyzed by GC. The results are given in Table 1 below.

TABLE 1

| Solvent | % Conversion | % Ring Bromination | % S-Oxidation |
| --- | --- | --- | --- |
| EDC | 33 | 20 | 80 |
| BCM* | 43 | 48 | 46 |
| Methanol | 32 | 0 | 100 |
| Pentane | <4 | trace | trace |

*BCM = bromochloromethane, about 6% product resulted from both s-oxidation and ring bromination.

As shown by the results in Table 1, ring bromination may compete with hetero atom oxidation depending upon the nature of the solvent. This is different from the use of anhydrous BrCl which leads only to ring brornination. With the stabilized aqueous bromine chloride reagent, the solvent polarity affects the course of the reaction. In the hydrocarbon solvents (pentane) there is no significant ring bromination or oxidation reaction. It is also apparent that using the BCM solvent (bromochloromethane) results in much more ring bromination than does EDC. In protic solvents (MeOH), ring bromination is totally absent because of the extremely fast oxidation rate of the sulfide moiety even under mild conditions. Even so, the use of the BrCl reagent according to the process of the invention causes very little over-oxidation to sulfones. This is in contrast to the widely used oxidizing agents, such as hydrogen peroxide, which require the use of moderating agents in order to avoid over-oxidation.

What is claimed is:

1. A process for oxidizing organic compounds, said process comprising reacting an organic compound which contains an oxidizable moiety, said moiety being selected from the group consisting of sulfide, phosphine, aldehyde, amine and selenide groups, with an aqueous oxidizing solution which comprises:

(a) water,
 (b) bromine chloride (BrCl), and
 (c) an inorganic halide salt which comprises a halide anion and a cation selected from the group consisting of alkali metal, alkaline earth metal, and transition metal cations, so as to insert at least one oxygen atom into said oxidizable moiety.

2. The process of claim 1 wherein said halide salt is a chloride salt and said solution contains a dichlorobromate anion and a cation selected from the group consisting of alkali metal, alkaline earth metal, and transition metal cations.

3. The process of claim 2 wherein said chloride salt is aqueous sodium chloride and said solution comprises aqueous $[Na^+(BrCl_2)^-]$.

4. The process of claim 1 wherein said solution contains from about 0.25 to 0.50 mole of bromine chloride per mole of halide salt.

5. The process of claim 4 wherein the bromine chloride ingredient in said solution constitutes from about 10 to 20 weight percent of said solution.

6. The process of claim 1 wherein the reaction is carried out in an organic solvent.

7. The process of claim 6 wherein said organic solvent is a polar solvent.

8. The process of claim 7 wherein said solvent is a protic solvent.

9. The process of claim 8 wherein said protic solvent is an alcohol.

10. A process for oxidizing organic compounds, said process comprising reacting an organic compound selected from the group consisting of sulfides and phosphines with an aqueous oxidizing agent solution which comprises:

(a) water,
 (b) bromine chloride (BrCl), and
 (c) a halide salt which comprises a halide anion and a cation selected from the group consisting of alkali metal, alkaline earth metal, transition metal, and quaternary ammonium cations, so as to insert at least one oxygen atom into said organic compound and provide, in the case of a sulfide, a sulfoxide or, in the case of a phosphine, a phosphine oxide.

11. The process of claim 10 wherein said halide salt is aqueous sodium chloride and said oxidizing agent solution comprises aqueous $[Na^+(BrCl_2)^-]$.

12. The process of claim 10 wherein said organic compound is a sulfide and the oxidized product is a sulfoxide.

13. The process of claim 12 wherein said organic compound is a thioether.

14. The process of claim 10 wherein said organic compound is a phosphine and the oxidized product is a phosphine oxide.

15. The process of claim 11 wherein said organic compound is an aryl thioether, the reaction is carried out in a protic organic solvent and the oxidized product is a sulfoxide.

16. The process of claim 15 wherein said organic compound is selected from thioanisole and methyl p-tolyl sulfide and said solvent comprises methanol.

17. The process of claim 11 wherein said organic compound is a phosphine, the reaction is carried out in an organic solvent selected from the group consisting of protic solvents, halohydrocarbon solvents and mixtures thereof, and the oxidized product is a phosphine oxide.

18. The process of claim 11 wherein said organic compound is selected from triphenyl-phosphine and neomenthyldiphenylphosphine.

* * * * *